United States Patent [19]

Clarke et al.

[11] Patent Number: 4,818,523

[45] Date of Patent: Apr. 4, 1989

[54] HAIR RINSE CONDITIONER

[75] Inventors: Jane Clarke, Matawan; Amrit Patel, Dayton; Clarence R. Robbins, Martinsville, all of N.J.

[73] Assignee: Colgate-Palmolive Company, Piscataway, N.J.

[21] Appl. No.: 63,194

[22] Filed: Jun. 17, 1987

[51] Int. Cl.$^4$ .............................................. A61K 7/08
[52] U.S. Cl. ..................................................... 424/70
[58] Field of Search .......................................... 424/70

[56] References Cited

U.S. PATENT DOCUMENTS

| | | | |
|---|---|---|---|
| 3,068,151 | 12/1962 | Haefele | 167/87.1 |
| 3,144,391 | 8/1964 | Goff | 167/87.1 |
| 3,216,983 | 3/1965 | Shelanski et al. | 260/88.3 |
| 3,579,629 | 5/1971 | Pasero et al. | 424/47 |
| 3,697,644 | 10/1972 | Laiderman | 424/70 |
| 3,808,051 | 4/1974 | Sato et al. | 134/2 |
| 3,876,760 | 4/1975 | Nersesian et al. | 424/70 |
| 3,925,542 | 12/1975 | Viout et al. | 424/47 |
| 3,928,558 | 12/1975 | Cheesman et al. | 424/47 |
| 3,959,461 | 5/1976 | Bailey et al. | 424/70 |
| 3,959,463 | 5/1976 | Nersesian | 424/70 |
| 4,144,326 | 3/1979 | Luedicke, Jr. et al. | 424/70 |
| 4,160,823 | 7/1979 | Watanabe et al. | 424/70 |
| 4,165,369 | 8/1979 | Watanabe et al. | 424/70 |
| 4,183,917 | 1/1980 | Iwao et al. | 424/70 |
| 4,210,161 | 7/1980 | Wagman | 132/7 |
| 4,220,166 | 9/1980 | Newell | 132/7 |
| 4,269,824 | 5/1981 | Villamarin et al. | 424/70 |
| 4,311,695 | 6/1982 | Starch | 424/184 |
| 4,374,825 | 2/1983 | Bolich et al. | 424/70 |
| 4,387,090 | 6/1983 | Bolich | 424/70 |
| 4,389,418 | 6/1983 | Burton | 424/365 |
| 4,421,740 | 12/1983 | Burton | 424/70 |
| 4,436,722 | 3/1984 | Matsunaga et al. | 424/70 |
| 4,472,375 | 9/1984 | Bolich et al. | 424/70 |
| 4,493,824 | 1/1985 | Abe | 424/70 |
| 4,610,874 | 9/1986 | Matravers | 424/70 |
| 4,777,037 | 10/1988 | Wagman et al. | 424/70 |

FOREIGN PATENT DOCUMENTS

| | | | |
|---|---|---|---|
| 727588 | 2/1966 | Canada | 167/73 |
| 0134998 | 3/1985 | European Pat. Off. . | |
| 1402017 | 5/1965 | France . | |
| 889291 | 2/1962 | United Kingdom . | |
| 1540862 | 2/1979 | United Kingdom . | |

OTHER PUBLICATIONS

Scott et al.; *Sorption of Quaternary Amonium Surfactants by Human Hair*; J. Soc. Cosmetic Chemists, 20, 135–152 (Feb. 5, 1969).

*Primary Examiner*—Ellis P. Robinson
*Assistant Examiner*—Susan S. Rucker
*Attorney, Agent, or Firm*—Richard J. Ancel; Murray M. Grill

[57] ABSTRACT

A stable easily removable hair rinse conditioner which provides good conditioning, styling ease, and manageability of hair, but does not build up with shampoo/anionic surfactants and is cost effective, consisting essentially of effective amounts of a dodecyl trimethyl quaternary ammonium compound, a saturated or unsaturated $C_{14}$–$C_{22}$ alkanol, and a cyclic or linear silicone, in an aqueous vehicle.

19 Claims, No Drawings

HAIR RINSE CONDITIONER

FIELD OF INVENTION

The present invention relates to a novel hair rinse conditioner which provides good conditioning, manageability, static control, ease of styling and is readily removable with conventional shampoos without build-up. The essential components of this composition are a dodecyl trimethyl quaternary ammonium compound, a $C_{14}-C_{22}$ saturated and/or unsaturated alkanol, and a cyclic or linear silicone, emulsified in an aqueous medium.

BACKGROUND AND PRIOR ART

When hair is washed with modern shampoos it is usually cleaned very efficiently, and the process not only removes soil, but also tends to remove the natural sebum which serves to lubricate the hair. This removal of lubrication increases the friction between the individual hair fibers and promotes tangling, both in wet and dry hair. It also gives rise to a build-up of static charge on the hair, particularly from interactions with plastic combs and brushes. The net result is damage to the hair. Also damage to the outer surface of hair is a continuous process caused by such factors as washing, brushing, atmospheric influences, etc. This continuing damage is very much associated with surface friction and any influence to reduce friction and static charge will also reduce the amount of damage to the hair.

The absorption onto hair of quaternaries having long chain fatty portions as part of its molecule is the basis for most hair conditioner formulae. The fatty portion of the molecule which is largely attached to the substrate acts as a lubricant. The lubricating action makes combing easier. However, this substantivity of said quaternary compounds to the hair dulls the hair and builds up on the hair.

It has been found that hair treated with a long chain fatty quaternary such as stearyl benzyl dimethyl ammonium chloride or cetyl trimethyl ammonium chloride or distearyl dimethyl ammonium chloride and the like, or a conditioner containing a fatty quaternary and then washed with a conventional shampoo containing anionic surfactants such as alkyl ether polyethenoxy sulfate (AEPS), sodium lauryl sulfate, and the like, has a deposit on its surface. This deposit is a combination product formed by the interaction of the shampoo anionic surfactant with the quaternary of the conditioner. Thus, it is difficult to remove the cationic quaternary with conventional shampoos containing anionic surfactants because of the formation of a cationic-anionic complex on the hair surface. Such deposit is not easily removed by conventional shampoo surfactants, and with continued use of the shampoo and the conditioner, the amount of this deposit or build-up tends to increase.

It has now been found that present novel hair rinse conditioners do not build-up on the hair, are easily removed from the hair by shampooing, and provide good conditioning and manageability.

In the field of hair conditioning, the prior art is replete with hair conditioing compositions containing one or more of the components of the present novel and unique no build-up hair rinse conditioner compositions. For example, U.S. Pat. No. 4,160,082 discloses compositions containing a stearyltrimethyl ammonium chloride conditioning agent and propylene glycol. U.S. Pat. No. 4,210,161 discloses a creme rinse containing cetyl trimethyl ammonium chloride and hydroxyethyl cellulose thickening agent. U.S. Pat. No. 4,436,722 discloses the combination of cetyl trimethyl ammonium chloride, cetyl alcohol and propylene glycol in hair conditioning compositions. U.S. Pat. No. 4,144,326 discloses an oil free hair rinse composition which includes the combination of lauryl trimethyl ammonium chloride, propylene glycol and hydroxypropylmethyl cellulose acidified with citric acid. U.S. Pat. No. 4,183,917 discloses an oil-in-water emulsion hair conditioning composition which comprises the combination of $C_{10}-C_{22}$ alkyl trimethyl ammonium chloride, mineral oil, cetyl alcohol and propylene glycol. In U.S. Pat. No. 4,421,740, a conditioning composition is disclosed which employs the combination of a mixed higher alkyl $C_{12}-C_{18}$ trimethyl ammonium chloride, cetyl or stearyl alcohol and hydroxyethyl cellulose. U.S. Pat. No. 4,374,825 discloses a hair conditioning composition containing the combination of a volatile silicone, a nonionic cellulose polymer thickening agent and a dicetyl dimethyl quat. or ditallow amine. European Pat. No. 0,137,998 discloses the combination of lauryl trimethyl quat and cetyl alcohol in a hair rinse composition. U.S. Pat. No. 4,220,166 discloses a moisture conditioner hair spray containing 1–15% of a 60:40% PVP-VA copolymer, and 0.05–1.5% of a copolymer of dimethyl polysiloxane and a polyoxyalkylene ester (Silicone Fluid SF1066 by GE) in alcohol. U.S. Pat. No. 3,928,558 discloses a hair spray composition containing cyclomethicone and a copolymer of vinyl pyrrolidone and vinyl acetate (PVP/VA) in a methylene chloride/isopropyl alcohol mixture. British Pat. No. 1,540,862 discloses that PVP/VA copolymers form an undesirable brittle film on the hair which causes unpleasant dusting and a dandruff-like condition, and is difficult to rinse off the hair.

However, it is noted that none of the above cited patents discloses a hair rinse conditioner composition which is easily removed from the hair, comprising the specific mixture of a dodecyl trimethyl halide, a $C_{14}-C_{22}$ alcohol or mixture of alcohols, and a cyclic or linear silicone, as the essential ingredients, emulsified in an aqueous medium.

SUMMARY OF THE INVENTION

It has been found that the treatment of hair with conditioners formulated with short chain cationics (specifically dodecyltrimethyl ammonium chloride (DTAC), results in hair which, surprisingly, is as conditioned as hair treated with longer chain cationics. The hair is easily combed, manageable and has no static flyaway. In addition, the shorter chain cationic conditioners are more easily removed from the hair, and do not cause shampoo build-up.

Dodecyltrimethyl ammonium chloride, in formulations with a higher fatty alcohol and a cyclic or linear silicone and other optional conditioner additives, gives good conditioning, styling ease and manageability of hair but does not build-up with shampoo/anionic surfactants as the longer chain cationic conditioning agents do.

Accordingly, a primary object of the present invention is to provide a hair rinse conditioner containing the short chain cationic ingredient, dodecyl trimethyl ammonium chloride conditioning agent, which is easily removed from the hair.

Another object of present invention is to provide a rinse conditioner which imparts superior conditioning effects, softness and manageability, static control, ease of combing and styling and does not cause shampoo build-up on the hair.

Another object of the present invention is to provide a stable, non-irritating, rinse conditioner capable of being applied daily after shampooing.

Another object of the present invention is to provide an economical hair rinse conditioner containing a minimum concentration of essential active ingredients.

Additional objects, advantages and novel features of the invention will be set forth in part in the description which follows, and in part will become apparent to those skilled in the art upon examination of the following specification or may be learned by practice of this invention.

To achieve the foregoing and other objects and in accordance with the present invention as embodied and broadly described herein, the stable novel hair conditioner composition of this invention consists of about 1.0% to 2.5% by weight of a dodecyl trimethyl quaternary ammonium compound, about 0.5 to 10% by weight of a $C_{14}$–$C_{22}$ alkanol or mixture of alkanols, and about 0.5 to 1.5% of weight of a cyclic or linear silicone, as the essential conditioning agents, in about 79% to 94.5 % by weight of an aqueous carrier. The final product is in the form of an emulsion and has a pH of about 3.0 to 4.0.

In a preferred aspect, the present invention relates to an easily removeable hair rinse conditioner composition with no build-up having a pH of about 3.0 to 4.0 consisting of, by weight, about 1.0% to 2.5% of a dodecyl alkyl trimethyl halide, and about 0.75 to 8.5% of a saturated or unsaturated $C_{14}$–$C_{22}$ alkanol or mixture of alkanols, and about 0.5–1.0 of a cyclomethicone or a dimethicone copolyol, as the essential ingredients, emulsified in 79% to 94.5% of deionized water.

The described hair conditioner compositions are stable, clear or opaque liquids at room temperature having a viscosity of about 3,000 to 5,500 cps and are in the form of a lotion type product. Further, these compositions are stable at 5 degrees C. to 60 degrees C. It is believed that these compositions are oil-in-water emulsions, with the quaternary compound and the alkanol supporting the emulsification properties and product stability.

As indicated, these compositions contain safe chemicals which are not irritating to the skin, are non-toxic and are effective to provide an easily removable conditioner with no shampoo build-up, and improve the manageability of the hair. The clear compositions have particular utility as extra light conditioners; whereas the opaque compositions are used as regular conditioners for normal hair, light conditioners for oily hair, high conditioning for dry hair, and as an extra body conditioner.

More specifically, additional preferred ingredients may be included in present novel hair conditioners for use on different types of hair, namely, oily, normal or dry hair, requiring heavy or light conditioning, or for extra body hair conditioners.

For example, the clear, extra light hair rinse conditioner of present invention comprises, by weight, about 2 to 2.5% dodecyltrimethyl quaternary ammonium compound, about 0.5 to 1.5% $C_{14}$–$C_{22}$ alkanol, preferably oleyl alcohol, about 0.5 to 1.5% of a silicone, preferably a dimethicone copolyol, and about 1 to 2% of a nonionic water soluble cellulose polymer in about 90 to 94.5% of an aqueous carrier. The cellulose polymer functions as a thickening agent and controls the viscosity of the composition.

The opaque light, regular and high conditioning hair conditioners comprise, by weight, about 1 to 2.5% dodecyl trimethyl quat, about 0.5 to 10% $C_{14}$–$C_{22}$ alkanol, about 0.5 to 1.5% silicone, about 0.5 to 1% propylene glycol, about 0.2 to 1.0% lanolin acetate, about 2 to 3% glyceryl monostearate, and about 1 to 5% mineral oil and/or petrolatum, emulsified in about 79 to 87.5% water. The propylene glycol functions as a solvent for the conditioning system. The lanolin acetate improves the flow and spreading properties of the conditioners on the hair. The glyceryl monostearate functions as a co-emulsifier with the quaternary compound. The mineral oil and petrolatum function as supplemental conditioning agents when additional conditioning of the hair is desired or necessary.

The opaque extra body hair conditioner of the present invention comprises, by weight, about 0.1 to 0.5% polyvinylpyrrolidone/vinyl acetate copolymer (PVP/VA) in addition to the ingredients set forth in the opaque light, regular and high conditioning hair conditioners set forth above. The PVP/VA provides extra body to the conditioner composition.

It is believed that the good conditioning properties are imparted to the hair when the composition is applied to the hair with or without subsequent rinsing due to the use of the essential mixture of conditioning agents, namely the dodecyl trimethyl quaternary compound, the $C_{14}$–$C_{22}$ saturated or unsaturated alkanol and the silicone. The supplemental petrolatum and mineral oil conditioning agents may be added where more conditioning is desired. Likewise, glyceryl monostearate may be added as a co-emulsifier with the quaternary compound and the alkanol. The viscosity and stability of the hair conditioner is controlled by the quaternary compound and the $C_{14}$–$C_{22}$ alkanol. However, a nonionic cellulose polymer may be added to thicken the composition when appropriate.

In addition, it has now been found that the present novel hair rinse conditioners are more readily and easily removed by shampooing with anionic surfactant-containing shampoo, resulting in no build-up of conditioner on the hair with extended use. A comparison with other formulae confirms that this is an unexpected and unusual property of the instant conditioners. It also has been found that tresses are shinier (cleaner) after treating with shampoos (which usually contain anionic surfactants such as sodium lauryl ether sulfate [SLES], triethanolammonium lauryl sulfate [TEALS] and sodium lauryl sulfate [SLS] and the like) and this rinse conditioner than similar tresses treated with the same type of shampoo and other conditioners.

DETAILED DESCRIPTION OF THE INVENTION

The short chain alkyl quaternary salt such as dodecyl trimethyl ammonium salt which is one of the essential compounds in the mixture of conditioning agents has been used in the prior art as a hair conditioning agent. It is a water soluble cationic surfactant also known as lauryl trimethyl ammonium salt, and has the following formula:

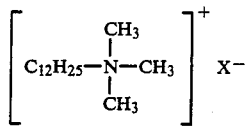

wherein X is a halide anion selected from the group consisting of chloride and bromide. The presence of the dodecyl trimethyl quaternary compound in the hair rinse conditioner improves wet and dry combing of the hair, reduces the static and controls fly-away of the hair, and supports emulsification of the composition.

The dodecyl trimethyl quaternary ammonium salts used in the present hair conditioning compositions may be obtained from a number of suppliers either in the form of a liquid or paste in an aqueous and/or isopropanol solvent at 25 degrees C or in the form of a solid. For example, the dodecyl trimethyl ammonium chloride purchased from Armak, as a 50% solution contains 50% A.I. (active ingredient) under the tradename Arquad 12-50. The dodecyl trimethyl ammonium salt is used in an amount of at least 1% and up to 2.5% by weight of the composition. It has been found that an amount less than 1% is insufficient to provide antistatic properties to the hair and to control fly-away of the hair treated therewith.

The second compound in the mixture of conditioning agents is a saturated or unsaturated $C_{14}$-$C_{22}$ alkanol, or a mixture of alkanols. Since the preferred alkanols are obtained from fats and oils, these alkanols are often referred to as fatty alcohols. However, alkanols made by synthetic processes also are satisfactory. Examples of suitable saturated alkanols are 1-tetradecanol, 1-hexadecanol, 1-heptadecanol, 1-octadecanol and mixtures of $C_{14}$-$C_{22}$ alkanols obtained by hydrogenating the fatty acids derived from tallow. Examples of unsaturated alkanols are oleyl alcohol (9,10 octadecanol). Preferred higher alkanols are stearyl alcohol, cetyl alcohol and oleyl alcohol and mixtures thereof. The proportion of $C_{14}$-$C_{22}$ alkanol present in the conditioner composition is about 0.5% to 10%, preferably 0.75% to 8.5%, by weight. Furthermore, the $C_{14}$-$C_{22}$ alkanol usually is the predominant compound in the mixture of conditioning agents because it is present in the largest percentage. $C_{14}$-$C_{22}$ alkanols function as co-emulsifying agents with the quaternary ammonium compound, thicken the emulsion, stabilize the product, and improve wet and dry combing of the hair.

The third essential component in the mixture of conditioning agents is a cyclic or linear silicone. More specifically, the silicone ingredient is selected from the group consisting of cyclomethicone and dimethicone copolyol. Cyclomethicone is a volatile cyclic silicone represented by the formula:

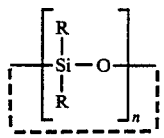

wherein R is a $C_1$-$C_3$ alkyl group or a phenyl group, preferably a methyl group; n is a number from 3 to 10, preferably 3 to 7, and the unsatisfied valencies on the oxygen and silicon atoms at the end of the chain are joined together to form a cyclic structure. Suitable cyclic silicones are available as low viscosity fluids from a number of manufacturers, including the General Electric Company. The most preferred cyclomethicones are decamethyl cyclopentasiloxane (General Electric's Silcone Fluid SF 1202) and octamethyl cyclotetrasiloxane (General Electric's Silicone Fluid SF 1173). The cyclic silicones are non-polar, insoluble in water and completely miscible in lower alcohols, aliphatic aromatic solvents and halogenated hydrocarbon solvents.

The linear silicone is a nonvolatile dimethicone copolyol, which is a stable polymer of dimethylsiloxane with polyoxyethylene and/or polyoxypropylene side chains, also known as dimethyl silixone-glycol copolymer, and is represented by the formula:

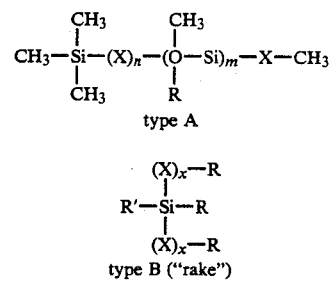

where, in both cases, R is a polyoxyethylene/polyoxypropylene chain, R' is a lower alkyl group and X is

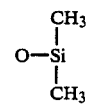

The values of x, m and n are not disclosed, but for type A materials, the weight ratios of polyoxyalkalene: dimethicone vary from 27:73 to 80:20 and the EO:PO ratio is usually 1:1.

Suitable linear silicones are available as clear liquids from a number of manufacturers, including the General Electric Company. The most preferred linear dimethicone copolyol is the copolymer of polydimethyl siloxane and a polyoxyalkylene ether (General Electric's Silicone Fluid SF 1188), which is soluble in cold water, but exhibits inverse solubility above 43 degrees C (110 degrees F.), is also soluble in acetone, toluene, lower alcohols and some hydrocarbons; has a viscosity of 1000 cps at room temperature (25 degrees C.) and a specific gravity of 1.04 and is a clear amber fluid. The linear silicone copolymers are nonionic and are soluble in lower alcohols. Their solubility in water varies, depending upon the ethylene oxide content. The silicone's function is to improve the wet combing of the hair. The amount of cyclic or linear silicone in the hair conditioner composition is about 0.5% to 1.5%, preferably 0.5% to 1.0% by weight.

The final essential ingredient in the hair rinse conditioner composition of present invention is an aqueous medium which is primarily water, preferably deionized water. Since the dodecyl trimethyl quaternary salts or the silicone may be supplied in admixtures with a $C_2$-$C_3$ alcohol, e.g. isopropanol, the aqueous medium may contain a small amount of said $C_2$-$C_3$ alcohol. Further, if desired, additional amounts of $C_2$-$C_3$ alkanol may be added to the composition, particularly where the composition is sold in the form of a "mousse." The proportion of the aqueous medium is in the range of 79% to 94.5%, by weight of the no build-up hair rinse composition.

Optionally, the hair conditioner composition may include mineral oil and/or petrolatum in the opaque conditioning compositions, as supplemental conditioning agents. Mineral oil is a homogeneous mixture of saturated aliphatic and alicyclic hydrocarbons derived from petroleum. Mineral oil is chemically and biologically inert and is hydrophobic in nature. Mineral oil is available in various viscosities. Petrolatum is a mixture of semi-solid hydrocarbons derived from petroleum, in the form of a jelly and is soluble in alcohol or chloroform. It is also chemically and biologically inert and is hydrophobic in nature. The proportion of mineral oil or petrolatum present in the hair rinse conditioner composition is about 1.0 to 5%, preferably 1.0 to 3%, by weight.

An optional ingredient in the clear hair rinse conditioning composition is a water-soluble, nonionic, cellulose polymer which functions as a thickening agent. Suitable cellulosic polymers are selected from the group consisting of hydroxyethyl cellulose and hydroxypropyl methyl cellulose, with hydroxyethyl cellulose being preferred. Hydroxyethyl cellulose is the product of reaction between an alkali cellulose and ethylene oxide, and such products are available in a number of viscosity grades. Viscosity is dependent upon the viscosity of the cellulose used in the reaction. The degree of substitution of hydroxyethyl groups per glucose unit is 1.4–1.5, the hydroxyethyl molar substitution is 1.5–3.0, and these hydroxyethyl celluloses have an average molecular weight range from about 80,000 to about 900,000. A particularly preferred hydroxyethyl cellulose is available under the tradename Natrosol 250 HR from Hercules, Inc.. Water-soluble hydroxypropyl methyl cellulose has a methyoxy content between about 25% and about 32% by weight and a hydroxypropyl content between about 2% and 10%, preferably 2% to 7%, by weight. Again, the chain length of the cellulose used in the reaction can be controlled to provide a molecular weight which yields a viscosity for a 2% solution in water in the range of 10 cps and 5000 cps, preferably 50 cps to 4000 cps.

These cellulose polymers provide stability to the composition upon aging by viscosity control. The composition retains its viscosity without thinning out or thickening. The proportion of nonionic cellulose polymer is about 0.1% to 2%, by weight of the clear hair conditioner composition.

Another optional ingredient in present hair conditioner composition, particularly in the extra body conditioner, is a hydroscopic nonionic copolymer of polyvinylpyrrolidone and vinyl acetate soluble in the lower alcohols. This PVP/VA copolymer has a specific affinity for the hair and the films formed thereon are generally adhesive, transparent, hard, lustrous and water-rewettable. PVP/VA is commercially available in proportions of 70/30, 60/40, 50/50, 45/55, and 30/70. Other PVP/VA copolymers include 20 to 60% PVP and 40 to 80% VA, commercially available as Luviskol 37E and Luviskol 281 (20% PVP and 80% VA). Polyvinylpyrrolidone/vinyl acetate is available in the form of a powder (contains about 95% polymer and 5% water), and in the form of a 25% and 50% solution in ethanol or isopropanol. PVP/VA E-735 is available from GAF as a clear liquid in a 50% solution of ethyl alcohol in the PVP/VA ratio of 70/30. The amount of polyvinylpyrroliddine/vinyl acetate is about 0.1 to 1%, preferably 0.2% to 0.5%, by weight of the final composition. Amounts of PVP/VA in excess of 1% by weight yield a film which is too rigid and too tacky.

Another optional ingredient in present novel conditioning composition is propylene glycol which is a clear, viscous, colorless liquid. It is hygroscopic and completely miscible with water. The propylene glycol functions as a solvent for the conditioning system. This ingredient may be included in either the opaque or clear rinse conditioners in accordance with present invention. The amount of propylene glycol in the composition constitutes about 0.5 to 1% by weight of the composition.

Another optional ingredient which may be included in the opaque conditioners of present invention is glyceryl monostearate, a monoester of glycerin and stearic acid having the general formula:

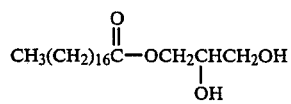

Glyceryl monostearate is a hard fat containing 30–40% of the alpha isomer, is dispersible in water, has a melting point of 54–60 degrees C. and is commercially available. This ingredient functions as a co-emulsifier with the quaternary compound and the fatty alcohol. The amount of glyceryl monostearate constitutes about 2 to 3% by weight of the composition.

Another optional ingredient which may be included in the opaque conditioners of the present invention is lanolin acetate which is an acetylated ester of an ethoxylated ether of lanolin alcohol having an average ethoxylation value of 10. Lanolin acetate is a liquid at room temperature, and improves the spreading properties of the conditioner on the hair. It is commercially available as Solulan 98 from the Amerchol Company, and is also known as Laneth-10 Acetate. The amount of lanolin acetate in the final composition constitutes about 0.2 to 1% by weight of the composition.

The pH of the hair rinse conditioner of present invention is acidic and ranges from about 2.5 to 4.5, preferably about 3 to 4. Suitable acids which may be used when needed are citric acid and the like.

The coaction of the three aforedescribed essential conditioning components unexpectedly provides a hair rinse conditioner product which is non-irritating, easily removed from the hair and does not cause shampoo build-up. The omission of a single component adversely affects the unique properties of the total composition. Accordingly, the criticality of the three ingredients and the specificity of each ingredient is necessary in the formulation of the present novel hair conditioning product. Furthermore, the present hair rinse conditioning composition not only provides an easily removable conditioner free of shampoo build-up on the hair but also provides easy styling, manageability, no static flyaway, and good wet and dry combing properties to the treated hair, and is more economical due to the use of minimal of the active ingredients (i.e. cost effective).

The hair conditioner compositions of this invention also may contain conventional additional components such as coloring agents, perfumes, preservatives such as formaldehyde (formalin) and Germaben 11 (Sutton Labs, Inc.) which is a clear liquid preservative system of 30% diazolidinyl urea, 11% methyl paraben (hydroxybenzoate) and 3% propyl paraben, in 56% propylene glycol; herbal extracts, and brighteners such as Uvinul. If the final product is filled into clear bottles, it has been found that the minimum amount of Uvinul necessary to obtain a color stabilized product is 0.02% by weight and up to 0.04% Uvinol. The use of opaque bottles does not require the presence of a brightener. The total weight of these optional additives usually does not exceed 5% by weight of the composition and preferably does not exceed 3% by weight of the composition, with the proportion of the individual ingredients often being 1% by weight or less.

The hair conditioner in accordance with the invention may be in the form of a pourable lotion or a smooth cream. Further, the final product may have any suitable viscosity so long as it is appropriate for the final form selected, e.g., a pourable lotion, a thick or viscous lotion or a cream.

The present hair rinse conditioner compositions can be manufactured readily by simple mixing methods. For example, a preferred method of preparing the present compositions comprises the steps of dispersing the cellulose polymer (hydroxyethyl cellulose), when used, in about one half of the formula amount of water and mixing while heating to 80-85 degrees C. until a uniform, clear, lump-free solution is obtained; adding the dodecyl trimethyl quaternary ammonium compound and the water soluble linear silicone with mixing while maintaining the temperature at 80-85 degrees C. to form a uniform aqueous solution; forming a separate mixture of the water-insoluble ingredients, $C_{14}-C_{22}$ alkanol or mixture of alkanols and the water insoluble cyclic silicone, wand the mineral oil, glycerol monostearate, petrolatum, when used, and heating said mixture to a temperature of about 80-85 degrees C.; adding the mixture of water-insoluble ingredients to the aqueous mixture with slow agitation; adding the remainder of the water with agitation which cools the resultant emulsion to about 50 degrees C.; adding the PVP/VA, the lanolin acetate and propylene glycol, when used, to the emulsion at about 50 degrees C.; cooling the resultant emulsion to 39 degrees C. with slow agitation; adding any other optional ingredients such as perfume, preservatives and herbal extracts to the foregoing mixture; and cooling the resultant composition to 25 degrees C. to 30 degrees C. in the presence of slow agitation to form a stable, opaque or clear emulsion having a pH in the range of 3.0 to 4.0 The final product is filled into opaque or translucent containers.

If a clear container is used, at least 0.02% and up to 0.5% Uvinol brightener is added to the formulation to prevent discoloration of the product.

The use of about one half of the formula amount of water at the end of the mixing process, decreases the cooling time, which speeds up the production and shortens the manufacturing time and saves energy. The use of the total amount of water at the beginning of the process takes a longer period of time to produce the formulation and uses more energy in the cooling operation, and is mroe costly.

The following examples merely illustrate the invention, but it is understood that the invention is not limited thereto. All amounts of various ingredients in the examples and elsewhere in the specification are by weight unless otherwise specified.

EXAMPLE 1

CLEAR EXTRA LIGHT HAIR CONDITIONER

| Ingredients | % |
| --- | --- |
| Deionized Water | 94.10 |
| Hydroxyethylcellulose | 1.35 |
| Silicone Copolymer (SF 1188 (GE)) | 0.75 |
| Oleyl Alcohol | 0.75 |
| DTAC (Lauryl Trimethyl Ammonium Chloride) | 2.25 |
| Germaben II (preservative) | 0.50 |
| Perfume | 0.30 |

In preparing the extra light hair conditioner of Example 1, the hydroxyethylcellulose is dispersed in one half of the formula amount of deionized water and mixed until a uniform clear solution is obtained and heated to 80-85 degrees C. with mixing. The lauryl trimethyl ammonium chloride and the silicone polymer are added to, and mixed with the aqueous hydroxyethyl cellulose solution at 80-85 degrees C. until a uniform aqueous solution is obtained. The oleyl alcohol, is heated to 80-85 degrees C. in a small mixer until a clear solution is obtained, which is slowly added to, and mixed with the aqueous solution at 80-85 degrees C. After addition is completed, the rest of the water is added to the emulsion mixture with mixing which cools the mixture to about 50 degrees C. The mixture is cooled to 39 degrees C. The perfume and Germaben II are added to the emulsion at 35-39 degrees C. with mixing and allowed to cool to room temperature. The final product is a clear pourable lotion which is stable under all conditions of aging.

The composition of Example 1 is readily spreadable and distributes well throughout the hair when applied directly to the hair using the fingers. Also, wet and dry combing are very good and the treated hair is manageable, easily styled and has no static flyaway. Further, the conditioners are easily removed from the hair with shampoo, and does not cause shampoo build-up on the hair. Maximum conditioning properties are obtained when the conditioner is applied to the hair without rinsing. Such use of this conditioner has application as a hair styling mousse.

EXAMPLE 2

LIGHT CONDITIONER FOR OILY HAIR

| Ingredients | % |
| --- | --- |
| Deionized Water | 87.50 |
| DTAC (Dodecyl Trimethyl Ammonium Chloride) (Armak) | 1.00 |
| Germaben II (preservative) (Sutton) | 0.50 |
| Cetyl Alcohol | 5.00 |
| Propylene Glycol | 0.50 |
| Cyclomethicone (SF 1202) (General Electric) | 1.00 |
| Glyceryl Monostearate (Tegin M) (Goldschmidt) | 2.65 |
| Lanolin Acetate (Solulan 98) (Amerchol) | 0.20 |
| Mineral Oil | 1.10 |
| Extrapon 5 special (Herbal extract)[1] (Dragoco) | 0.25 |
| Perfume | 0.30 |

[1]Herbal Extract Mixture, a product of Dragoco, Inc.
This composition is an opaque, lotion type product with viscosity of 4500 +/− 1000 cps and pH 3.5 +/− 0.5.

The hair conditioner for oily hair of Example 2 is prepared by dissolving the dodecyltrimethyl ammonium chloride and propylene glycol in deionized water at 80-85 degrees C. The water insoluble ingredients, cetyl alcohol, cyclomethicone, glyceryl monosteraate, and mineral oil are slowly mixed and heated at 80-85 degrees C. in a small mixer until a uniform clear solution is obtained which is slowly added to, and mixed with the aqueous solution at 80-85 degrees C. After addition is completed, the emulsion mixture is cooled to about 50 degrees C. and the lanolin acetate is added thereto with mixing and further cooled to about 35 degrees C. The Germaben II, perfume and the herbal extract are added to the emulsion with mixing and allowing to cool to room temperature.

The final product is stable under all conditions of aging and provides excellant conditioning properties including combability; manageability, and no static flyaway and is easily removed with no conditioner/anionic shampoo build-up on the hair.

EXAMPLE 3

REGULAR CONDITIONER FOR NORMAL HAIR

| Ingredients | % |
| --- | --- |
| Deionized Water | 82.05 |
| DTAC (Dodecyl Trimethyl Ammonium Chloride) (Armak) | 1.75 |
| Germaben II (preservative) (Sutton) | 0.50 |
| Cetyl Alcohol | 4.50 |
| Propylene Glycol | 0.50 |
| Cyclomethicone (SF 1202) (General Electric) | 1.00 |
| Glyceryl Monostearate | 2.40 |
| Lanolin Acetate (Solulan 98) (Amerchol) | 0.50 |
| Mineral Oil | 1.50 |
| Stearyl Alcohol | 2.50 |
| Petrolatum | 2.50 |
| Perfume | 0.30 |

This composition is an opaque lotion type product, with viscosity of 4000 +/− 1000 cps and pH 3.5 +/− 0.5.

This composition is prepared in accordance with the process of Example 2 except that the petrolatum and stearyl alcohol are added to the water insoluble mixture of ingredients; and the herbal extract is omitted.

The final product is also stable upon aging and provides very good conditioning properties and does not build-up on the hair after numerous washing and conditioning steps.

EXAMPLE 4

HIGH CONDITIONING FOR DRY HAIR

| Ingredients | % |
| --- | --- |
| Deionized Water | 79.37 |
| DTAC (Lauryl Trimethyl Ammonium Chloride) | 1.75 |
| Germaben II (preservative) | 0.50 |
| Cetyl Alcohol | 5.40 |
| Propylene Glycol | 0.50 |
| Cyclomethicone (GE 1202) | 1.00 |
| Glyceryl Monostearate | 2.88 |
| Lanolin Acetate | 0.50 |
| Mineral Oil | 1.80 |
| Stearyl Alcohol | 3.00 |
| Petrolatum | 3.00 |
| Perfume | 0.30 |

The composition is prepared in accordance with the precess of Example 3, using greater quantities of the conditioning ingredients cetyl alcohol, stearyl alcohol, mineral oil and petrolatum, and glyceryl monostearate.

This final product provides a high conditioning properties, without causing build-up on the hair of conditioner/anionic shampoo.

EXAMPLE 5

EXTRA BODY HAIR CONDITIONER

| Ingredients | % |
| --- | --- |
| Deionized Water | 87.20 |
| DTAC (Lauryl Trimethyl Ammonium Chloride) | 1.00 |
| Germaben II (preservative) | 0.50 |
| Cetyl Alcohol | 5.00 |
| Propylene glycol | 0.50 |
| Cyclomethicone (SF 1202) (General Electric) | 1.00 |
| Glyceryl Monostearate | 2.65 |
| Lanolin Acetate (Solulan 98) | 0.20 |
| Mineral Oil | 1.10 |
| PVP-VA E735 (GAF) | 0.30 |
| Extrapon 5 special (Herbal Extract) (Dragoco) | 0.25 |
| Perfume | 0.30 |

The composition is an opaque, lotion type product with a viscosity of about 4500 +/− 1000 cps and pH 3.5 +/− 0.5.

This composition is prepared in accordance with the process of Example 2, except that the polyvinyl pyrrolidone-vinyl acetate copolymer is added to the partially cooled emulsion prior to the addition of the perfume and preservative.

The presence of the PVP/VA provides extra body to the hair conditioner.

Laboratory experiments were run to evaluate wet and dry combing properties of hair treated with the conditioners of present invention compared to commercial conditioners.

Three gram tresses were prepared from either 10" Oriental hair or 10" dark brown European hair and washed with 20% triethanol ammonium lauryl sulfate and air dried prior to treatment. Each tress was wet out with tap water, and then treated with 2.5 ml conditioner which was rubbed into the tress for 30 seconds. The tresses were then combed 10 comb strokes and rinsed under the running tap for 30 seconds at approximately 105 degrees F. The tresses were then combed both wet and dry by panelists and ranked for ease of combing. The data was evaluated by the Friedman nonparametric statistical test.

Conditioner of Example 3 vs. Commercial Conditioner A (Containing SACL). Expert combing panelists determined Example 3 to be significantly better than Conditioner A.

Conditioner of Example 2 vs Commercial Conditioner B (containing SACL). Example 2 significantly better.

Conditioner of Example 2 vs Commercial Conditioner A. Example 2 significantly better than Commercial Conditioner A.

Conditioner of Example 3 vs. Commercial Conditioner C-(containing SACL). Example 3 better wet combing than Conditioner C.

All of these differences were significant at 95% confidence level. Dry combing was judged to be good and no static flyaway condition was seen.

The similarity in chemical and physical behavior of the hair and wool keratin fibers aids in the studies of hair sorption of particular ingredients. Accordingly, a wool swatch dye test was used to investigate removal of conditioner and build-up on the hair.

In the wool swatch dye test, two wool swatches, 3 by 4.5 inches, weighing about 1 gm each (wool challis from Test Fabrics Inc., Middlesex, N.J.) are wetted out under running tap water at about 105 degrees F. 5 ml of 1 to 2% of the test conditioners are applied to and rubbed into the swatches for 60 seconds. The treated wool swatches are washed with 5 ml of 10% sodium decyl ether sulfate by rubbing lather into the swatches for 60 seconds, then rinsed under tap water for 60 seconds. The swatches are immersed into a beaker containing 40 1 of a 0.5% Red 80 dye solution for 30 seconds and then rinsed under running tap water for 30 seconds, and dried on a rack at room temperature. If the cationic component of the conditioner remains on the swatch, the swatch will stain red to pink.

The results of the wool swatch/dye test indicate that nearly all the dodecyl trimethyl ammonium chloride (DTAC) alone or in a conditioner, is removed from the wool swatch by washing with the anionic used in a shampoo, compared to complexation and incomplete removal for longer chain cationics e.g. Stearalkonium chloride (SACL), and Cetyl Trimethylammonium chloride (CTAC). This clearly indicates no build-up of present conditioners on the hair.

The single fibre experiment also shows that conditioner/wash cycles of DTAC/triethanolammonium lauryl sulfate (TEALS), do not cause scale after 3 cycles to uplift after one cycle of SACL/TEALS. This indicates no formation of cationic-anionic complex to cause scale raising in the DTAC conditioners of present invention.

Radiolabel experiments were also used to investigate removability and build-up of the conditioners of present invention in comparison to long chain quaternary compounds.

The test compounds [14C] Stearalkonium chloride and cetyl trimethyl ammonium chloride were synthesized along with [35S] ammonium lauryl sulfate (ALS). Sodium Lauryl Sulfate [35S] (SLS; activity=0.30 microcuries per ml) is also substituted for ALS.

The above compounds were diluted with their non-radioactive counterparts to make final solutions of 1.69% CTAC in $H_2O$, 5% ALS in $H_2$, and 1% SACL in 30:70 ethanol/water. The final activities of the test solutions were 0.15 microcuries per ml for CTAC, 0.30 microcuries per ml for ALS, and 0.075 microcuries per ml for SACL. Dodecyltrimethyl ammonium chloride (DTAC) having an activity of 0.2 microcuries per ml is also prepared.

Wool swatches were prepared for radiolabelling experiments by treating the swatches, which weighed roughly 1.5 grams, with 3 ml of 20% triethanolammonium lauryl sulfate (TEALS), rubbing by hand for 2 minutes, and then rinsing under 100 degrees F. running tap water for an additional 2 minutes.

Following overnight drying, the washed swatches were cut with a pair of pinking shears into 0.14 gram segments having areas of approximately 1.3 square inches and put aside for use in binding experiments involving the above radiolabelled compounds. In general, five swatches were prepared for each treatment being studied.

In all binding experiments, stainless steel wire gauzes with rectangular holes cut slightly smaller than the test swatches were placed over beakers. A test swatch was then wetted with tap water, excess water squeezed out, and the swatch then placed over the hole. Following this, 0.3 ml of a test solution was applied as evenly as possible to all areas of the wool which was then rubbed for one minute between two lengths of rubber tubing mounted on metal rollers.

After rubbing, the wool swatches were rinsed in a beaker of tap water for 45 seconds, followed by a 15 second rinse in a second beaker. A final rinse was then performed for 1 minute under 100 degrees F. running tap water.

Depending upon the particular experiment, after the above treatment, wool swatches could either be hung up to dry or else treated again following the squeezing out of excess water using rubber tubing placed over the ends of crucible tongs.

Following treatment and drying, wool swatches were dissolved by placing each in a counting vial, adding 1 ml of 2M NaOH, and heating in an oven for 1.5 hours. Three reference vials were also prepared in which a wool swatch was dissolved following addition of a known amount of the radiolabelled compound being tested.

Following cooling, roughly 12 ml of Aquasol-2 LSC Cocktail was added to each vial, followed by addition of 0.250 mL of concentrated perchloric acid. The vials were then shaken vigorously resulting in a clear solution ready for counting.

The results of the radiolabel experiments are:

(1) 2% DTAC/4.85% SLS (hot): $2.78+/-0.31$ mg/g wool compared to $4.09+/-0.57$ mg/g for 1% SACl/4.8% ALS (hot). Hot SLS binds $2.31+/-0.24$ mg/g wool but hot ALS alone binds $1.94+/-0.18$ mg/g. Similarly 1.69% CTAC/5% ALS binds $4.93+/-1$ mg/g of wool. With the longer chain quats more anionic is bound to the wool (building up) than with the shorter chain DTAC.

(2) Example 3 DTAC conditioner/Hot SLS (5%): binds 1.93 mg/g SLS to wool. Commercial Conditioner A (active is SACL)/5% (hot) ALS binds $4.03+/-0.54$ mg/g of wool. For Commercial Conditioner C (another SACL based conditioner)/5% hot ALS, $3.05+/-0.31$ mg/g of wool is bound. Hence, the conditioner with the shorter chain cationic does not bind as much anionic to it i.e. more is removed and it does not build up on the surface.

(3) For cyclic treatment of wool with DTAC conditioner of Example 3/Hot SLS (4.7%), the amounts of bound SLS after 1, 2, and 3 cycles are $1.3+/-0.2$, $1.77+/-0.3$, and $2.08+/-0.2$ mg/g wool compared to values of $3.95+/-0.3$, $4,82+/-0.9$ and $5.03+/-0.6$ for a Commercial Conditioner A/Hot ALS system. Hence the values for the shorter chain DTAC system are lower and it is not building up as much as the longer chain cationic in Commwercial Conditioner A i,e. SACL.

It is understood that the foregoing detailed description is given merely by way of illustration and that variations may be made therein without departing from the spirit of the invention.

We claim:

1. A stable easily removable hair rinse conditioner composition comprising about 1.0 to 2.5% by weight of a dodecyl trimethyl quaternary ammonium compound, about 0.5 to 10% by weight of a $C_{14}$-$C_{22}$ alkanol or mixture of alkanols, and about 0.5 to 1.5% by weight of a cyclic or linear silicone, in about 79 to 94.5% by weight of an aqueous carrier, said composition being in the form of an emulsion and having a pH of about 2.5 to 4.5.

2. A composition according to claim 1, wherein said quaternary compound is a lauryl trimethyl ammonium halide.

3. A composition according to claim 2, wherein said quaternary compound is lauryl trimethyl ammonium chloride.

4. A composition according to claim 1, wherein the alkanol is a saturated or unsaturated $C_{14}$–$C_{22}$ alkanol or mixture of alkanols.

5. A composition according to claim 1, wherein said silicone is a cyclomethicone or a dimethicone copolyol.

6. A composition according to claim 1, also containing about 1% to 2% by weight of a nonionic water soluble cellulose polymer.

7. A composition according to claim 6, which is a clear extra light hair rinse conditioner and said cellulose polymer is hydroxyethyl cellulose and said linear silicone is a methicone polyol.

8. A composition according to claim 1, also containing about 1 to 5% by weight mineral oil and/or petrolatum as additional conditioning agents.

9. A composition according to claim 8, which is an opaque hair conditioner also containing, by weight, about 0.5 to 1% propylene glycol, about 0.2 to 1.0% lanolin acetate and about 2 to 3% glyceryl monostearate.

10. A composition according to claim 8, which is an extra body hair conditioner, also containing about 0.1 to 0.5 by weight polyvinyl pyrrolidone/vinyl acetate copolymer.

11. A composition according to claim 9, which is an opaque light conditioner for oily hair wherein the alkanol is about 5% cetyl alcohol and the cyclic silicone is cyclomethicone.

12. A composition according to claim 9, which is an opaque regular conditioner for normal hair, wherein the alkanol constitutes about 7% by weight of a mixture of cetyl alcohol and stearyl alcohol, and the cyclic silicone is cyclomethicone.

13. A composition according to claim 9, which is an opaque high conditioner for dry hair wherein the alkanol constitutes about 8.5% by weight of a mixture of cetyl alcohol and stearyl alcohol, and the cyclic silicone is cyclomethicone.

14. A conditioner for dry hair according to claim 13, consisting by weight, of about 1.75 lauryl trimethyl ammonium chloride, about 5.5% cetyl alcohol and 3% stearyl alcohol, about 0.5% propylene glycol, about 1% cyclomethicone, about 2.9% glyceryl monostearate, about 0.5% lanolin acetate, about 1.8% mineral oil and 3% petrolatum emulsified in about 80% deionized water.

15. A conditioner for oily hair according to claim 11, consisting by weight, of about 1% dodecyl trimethyl ammonium chloride, about 5% of cetyl alcohol, about 0.5% propylene glycol, 2.65% glyceryl monostearate, about 1% cyclomethicone, about 0.2% lanolin acetate, and about 1.1% mineral oil emulsified in about 87.5% deionized water.

16. A conditioner for normal hair according to claim 12 consisting by weight, of about 1.75% of dodecyl trimethyl ammonium chloride, about 4.5% of cetyl alcohol and 2.5% stearyl alcohol, about 0.5% propylene glycol, about 1% cyclomethicone, about 2.4% glyceryl monostearate, about 0.5% lanolin acetate, and about 1.5% mineral oil and 2.5% petrolatum, emulsified in about 82% of deionized water.

17. An extra body conditioner according to claim 10, consisting by weight, of about 1% dodecyl trimethyl ammonium chloride, about 5% cetyl alcohol, about 0.5% propylene glycol, about 1% cyclomethicone, about 2.65% glyceryl monostearate, about 0.2% lanolin acetate, about 1.1% mineral oil and about 0.3% polyvinyl pyrrolidone-vinyl acetate copolymer, emulsified in about 87.2% deionized water.

18. A clear extra light conditioner according to claim 7, consisting, by weight, of about 1.35% hydroxyethyl cellulose, about 0.75% of the linear dimethicone polyol copolymer, about 0.75% oleyl alcohol and about 2.25% lauryl trimethyl ammonium chloride, dispersed in about 94% deionized water.

19. A composition according to claim 1 wherein the pH ranges from 3.0 to 4.0

* * * * *